United States Patent [19]
Jakkula et al.

[11] Patent Number: 6,012,324
[45] Date of Patent: Jan. 11, 2000

[54] METHOD FOR MEASURING GAS CONTENT AND A GAS CONTENT MEASURING DEVICE

[75] Inventors: Pekka Jakkula, Oulu; Urpo Kasurinen, Tampere; Rauli Virkkala; Jouko Niinimäki, both of Oulu, all of Finland

[73] Assignee: Valmet Automation Inc., Helsinki, Finland

[21] Appl. No.: 09/081,362

[22] Filed: May 19, 1998

[30] Foreign Application Priority Data

May 21, 1997 [FI] Finland ..................................... 972172

[51] Int. Cl.[7] ............................ G01N 29/00; G01R 27/04
[52] U.S. Cl. ............................................ 73/19.03; 324/640
[58] Field of Search .............................. 73/19.03, 861.04, 73/19.1; 324/640, 639, 637

[56] References Cited

U.S. PATENT DOCUMENTS 4,852,395  8/1989  Kolpak ................................. 73/61.1 R
5,502,393  3/1996  Yamaguchi et al. .................... 324/639

FOREIGN PATENT DOCUMENTS 0084299  7/1991  Finland .

OTHER PUBLICATIONS

WPI/Derwent Abstract, No. 97–499438, Week 9746 of JP 9236555.

Primary Examiner—Hezron Williams
Assistant Examiner—Jay L. Politzer
Attorney, Agent, or Firm—Ladas & Parry

[57] ABSTRACT

The invention relates to a method for measuring gas content in a fluid, such as papermaking pulp or coating paste, and to a gas content measuring device. Pressure variations generated by a pump, for instance, are to occur in the fluid. Travel time, phase and/or attenuation of the microwave signal (20) are measured with the gas content measuring device while the signal (20) penetrates through the fluid (13), and the gas content is determined on the basis of changes in travel time, phase and/or attenuation of the microwave signal (20) caused by pressure variations of the fluid (13).

21 Claims, 3 Drawing Sheets

METHOD FOR MEASURING GAS CONTENT AND A GAS CONTENT MEASURING DEVICE

FIELD OF THE INVENTION

The invention relates to a method for measuring the gas content of a fluid, in which pressure variations occur.

The invention also relates to a gas content measuring device that is arranged to measure gas content in a fluid, in which pressure variations occur.

BACKGROUND OF THE INVENTION

At present, methods and devices based on ultrasound and density measuring are mainly used for measuring the gas content, and particularly the air content, of a fluid or liquid. In ultrasound measuring, the ultrasound is transmitted through the fluid to be measured and its attenuation is measured. The attenuation of the ultrasound is a function of the gas content in the fluid, so the more there is gas in the fluid, the more the ultrasound attenuates. In paper industry, the gas content of papermaking pulp or stock is typically measured by means of ultrasound measuring. The quality of the end product, i.e. paper, depends on the quality of the fluid papermaking pulp which is partly defined by its gas content.

Finnish Patent 84,299 discloses a solution, in which the air content of a suspension is determined by measuring the water content of the suspension at two different known pressures. U.S. Pat. No. 4,852,395 also discloses a solution, in which the gas content of a flowing liquid is determined by measuring the transmissivity of microwave radiation through the liquid at two different known pressures.

One problem with the gas content measuring based on the ultrasound attenuation is, however, that the method cannot be applied to suspensions containing considerably solid matter. For instance, the gas content measuring of pulp used for paper making can be done only, if the pulp consistency is less than 2%. Moreover, it is difficult to apply the method for installations of in-line type. This is why the ultrasound measuring devices have generally been developed for measuring a sample flow corresponding as closely as possible to pulp. On the other hand, one problem with the density measuring is that the measurement is also very sensitive to other components than air, which cause changes in concentration. Air is the most common gas in papermaking pulp. In papermaking pulp, typical density values of different suspension components are the following: water=1, air=0, wood fiber=1.3 to 1.5, and fillers=2.5 to 4.5. These figures show that even a slight decrease in filler amounts in pulp gives the impression that the air content of pulp has inreased.

The problem with microwave measurings carried out at two known pressures is that pressures employed have to be measured exactly at the point where the microwave measuring is also carried out. The pressure indicator is to be accurately calibrated to avoid systematic measuring errors in gas content.

BRIEF DESCRIPTION OF THE INVENTION

The aim of the invention is thus to develop a method and an equipment for implementing the method to the effect that the above problems can be solved. The method and the measuring device in accordance with the invention can also be applied to a suspension with a consistency exceeding 2%. The solution in accordance with the invention is also insensitive to different densities of various components of a fluid or suspension.

This is achieved with a method described in the preamble, the method being wherein measuring is effected with a microwave signal, and at least one variable of the microwave signal is measured after the microwave signal has penetrated through a fluid, and the gas content of the fluid is determined on the basis of changes that pressure variations have caused to said variable of the microwave signal.

A gas content measuring device in accordance with the invention is wherein the gas content measuring device comprises a microwave meter, a transmitting antenna and a receiving antenna, which are arranged to measure at least one variable the microwave signal while the signal penetrates through a fluid, and the gas content measuring device comprises means for determining the gas content in a fluid on the basis of changes that pressure variation has caused to said variable of the microwave signal.

Several advantages are achieved with the method and system of the invention. The solution in accordance with the invention also enables the measuring of gas content in high-consistency suspensions without problems resulting from different densities of the components of the suspension.

BRIEF DESCRIPTION OF THE DRAWINGS

In the following, the invention will be described in greater detail by means of preferred embodiments with reference to the accompanying drawings, in which.

DETAILED DESCRIPTION OF THE INVENTION

The invention is suited for measuring gas content in various fluids, e.g. liquids and suspensions, in which pressure variations occur. The invention is particularly well suited for paper making, without being restricted thereto, however.

Figure 1:
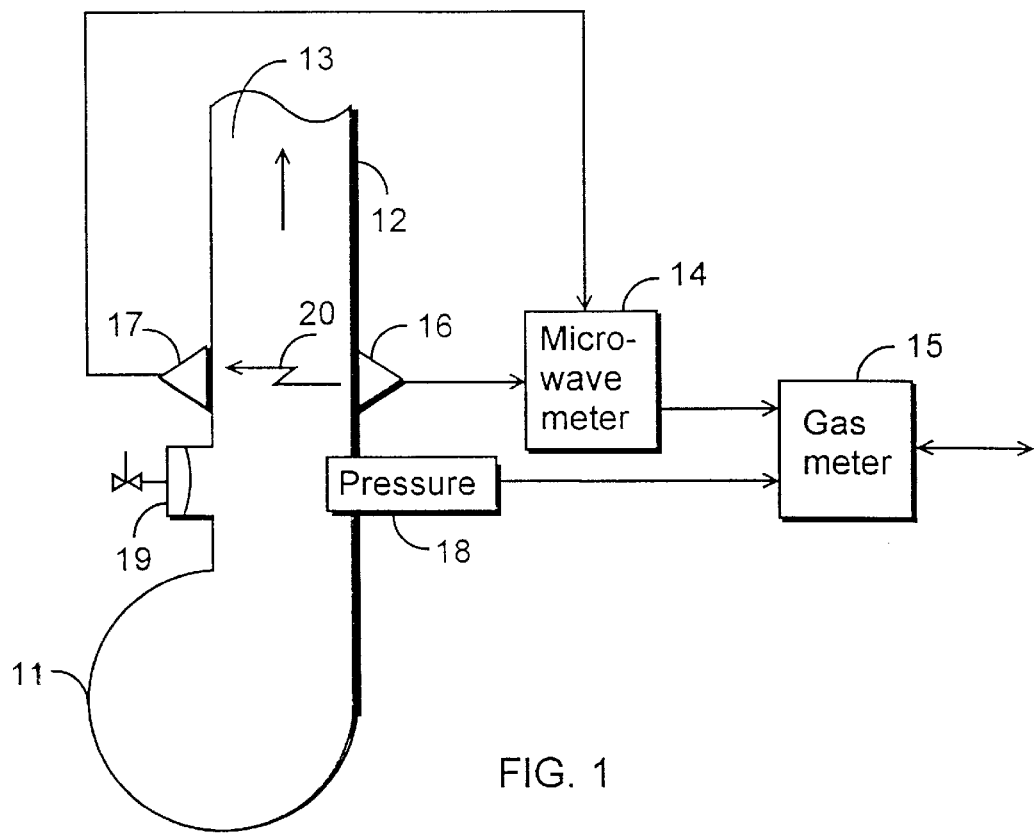
FIG. 1 illustrates an arrangement for measuring gas content.

The method and typical measuring arrangement of the invention are now examined by means of FIG. 1. The arrangement in accordance with FIG. 1 comprises a pump 11, a duct 12, a fluid 13, a microwave meter 14, means 15 for determining gas content, a transmitting antenna 16 and a receiving antenna 17. In addition, the arrangement may comprise a pressure indicator 18 and a pressure modulator 19. The pump 11 pumps fluid 13, and as a consequence, the fluid flows in the duct 12. The operation of the pump 11 typically causes changes of pressure in the fluid 13. If the fluid 13 contains air, or in a general case, a gaseous substance reacting at least nearly like an ideal gas, the rise in pressure makes the gaseous substance compress. On the other hand, when the pressure is restored to a lower level, the gaseous substance expands back to its former volume. In a typical fluid 13, like a suspension containing wood fibers, no other components compress substantially, apart from gas. Thus the degree of compression indicates the air or gas content of the fluid.

In the solution of the invention, a microwave signal 20 is used for measuring the amount of gas, the microwave signal being transmitted via the transmitting antenna 16 through the fluid 13 to the receiving antenna 17. The microwave meter 14 measures from the microwave signal 20 some of the following variables: signal phase, travel time, or attenuation while the signal 20 passes through the fluid 13.

First is examined mainly the signal travel time, which corresponds, in a general level, to the phase measuring, since changes in phase result from changes in signal travel time. The means 15 determine the gas content of the fluid 13 on the basis of the changes in travel time. If the duct 12 contains gasfree liquid 13, for instance, water, the pressure variations caused by the pump 11 have no effect on the volume of the fluid 13. Then the travel time of the microwave signal remains unchanged in spite of pressure variations. But if the fluid 13 contains gas, volumetric changes in gas produce changes in the travel time of the microwave signal 20. The microwave signal 20 travels faster in gas than in liquid, so the higher the gas content in the fluid 13, the faster the microwave signal passes through the fluid 13. Thus under the effect of high (momentary) pressure in the duct 12, the microwave signal travels a shorter distance in gas, since the gas is compressed, and consequently the signal travels from the transmitting antenna 16 to the receiving antenna 17 slower than at low (momentary) pressure. A change in the microwave travel time also changes a signal phase, and hence the change can be seen as phase changes caused by the pressure. The purpose of the method of the invention is to measure the difference between the longest and shortest travel time, and hence indirectly to deduce the degree of the compression of the gas, and further, to deduce from the degree of the compression the amount of gas, since a great amount of gas compresses, absolutely measured, more than a small amount. When the absolute level and variation of the pressure are preferably predetermined, and liquids containing no solid particles are measured, the amount of gas can be directly deduced on the basis of the highest and lowest value of the microwave signal travel time.

The signal travel time can be directly measured by measuring the time it takes for the signal to pass through the fluid. However, this kind of procedure is technically difficult to realize. Moreover, since the changes in travel time are important in view of the invention, not the travel time itself, the measuring of changes in travel time is advantageously performed by measuring the phase changes of the signal.

The pressure indicator 18 can be utilized in two different ways. The static pressure can be measured with the pressure indicator 18, and from that the actual amount of gas in the process can be determined. The measuring of the amount of gas in accordance with the invention indicates the amount of air at the pressure at which the measuring is carried out. By means of the pressure indicator 18 the actual pressure in the process is known, and hence the absolute amount of gas can be calculated in unpressurized state. The dynamic pressure can also be measured with the pressure indicator 18. Since changes in component proportions of the process affect the microwave measuring, it is important that a distinction can be made between the changes resulting from the gases in the process, and the changes resulting from changes in consistency or component concentration.

Particularly in suspensions, the travel time, phase and attenuation of the microwave signal also depend on the consistency of the suspension, however. Thus in the solution of the invention, the consistency of the suspension is measured. The consistency can be measured by means of any known method, but most preferably the measuring of consistency is performed with the same microwave meter as the measuring of gas content. Thus the device of the invention is adjusted to measure consistency by means of the microwave travel time. Frequency modulation in accordance with the FMCW technique (Frequency Modulated Continuous Wave) is used for measuring. In the FMCW technique, the oscillator frequency is linearly scanned on a broad band like in radar, with a sinusoidal signal at the mixer output. The frequency of this signal indicates the difference in travel time between the reference signal and the received signal, the difference being affected by consistency, for instance. The consistency typically changes in all liquid and suspension processes slower than, for instance, pressure variation produced by the pump 11. Then the consistency can be measured as a long term average on the basis of the travel time, whereas the gas content is measured, for instance, by the phase measuring based on the travel time in the considerably shorter term (typically less than 1 s) without frequency modulation. In the method of the invention, a separate pressure indicator 18 can be further utilized for essentially measuring the pressure level and the real variation in the travel area of the microwave signal 20. When the exact pressure and its real variation are known, whether the pressure variates considerably or irregularly, it is possible to determine the amount of gas on the basis of the travel time of the microwave signal 20. Thus, for instance, a correlation between the pressure variation measured with the pressure indicator 18 and the travel time variation (phase variation, attenuation variation) measured with the microwave meter 14 can be calculated. A correlation $C(\tau)$, in which $x(t)$ is the pressure as a function of time (t) and $y(t)$ is the travel time (phase, attenuation) of the microwave signal as a function of time, is calculated, for example, with the formula $C(\tau)=\int x(t)y(t-\tau)dt$. By means of the correlation, pressure variations can be distinguished from other factors, such as changes in consistency, affecting the travel time (phase, attenuation).

Figure 2:
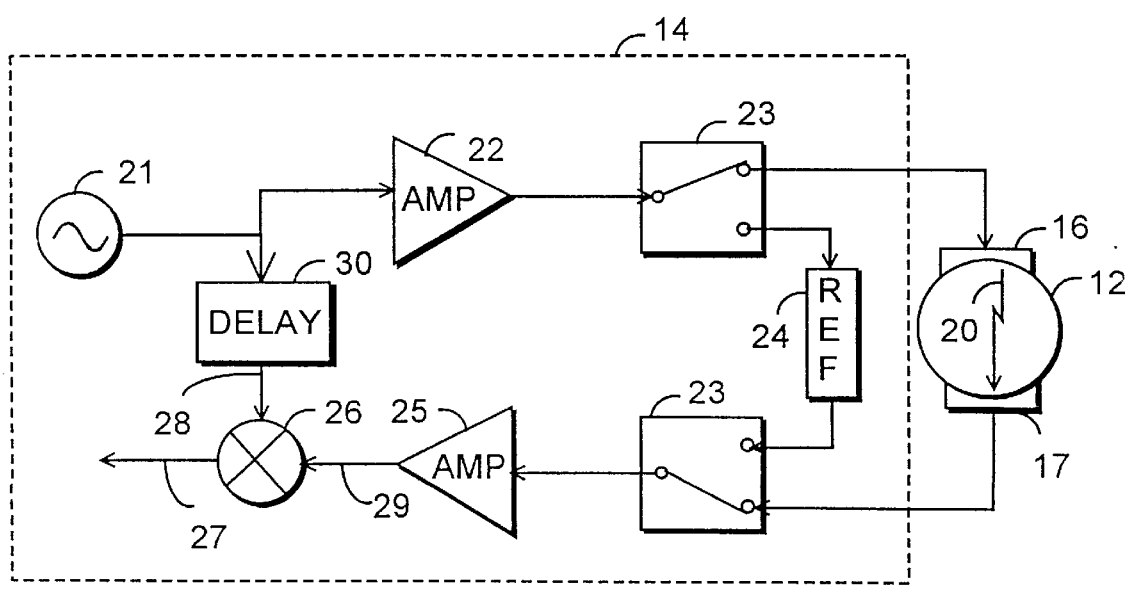
FIG. 2 illustrates a circuitry of a gas content measuring device when a phase of a microwave signal is measured.

In the following, the solution in accordance with the invention, based on phase measuring, is examined in greater detail with the help of FIG. 2, the solution comprising, with relation to a microwave meter 14, a local oscillator 21, a transmitter amplifier 22, switches 23, a reference channel 24, a receiver amplifier 25 and a mixer 26. Moreover, the figure comprises a transmitting antenna 16, a duct 12 and a receiving antenna 17. The oscillator 21 transmits microwave frequency both to the transmitter amplifier 22 and the mixer 26. After the transmitter amplifier 22 has amplified the oscillator 21 signal, it is selected with the switch 23, whether the signal is transmitted to the duct 12 for the actual process measuring, or whether the measuring is performed on the reference channel 24, by means of which drifting of the amplifiers can be monitored and compensated. The reference channel is typically a transmission line, such as a coaxial cable or a strip line, whose travel time and attenuation remain stable at various temperatures in the long term. After the signal has passed either through the actual process measuring in the parts 16, 12 and 17, or on the reference channel 24, the signal is selected with the switch 23 to the receiver amplifier 25. From the receiver amplifier 25 the signal propagates further to the mixer 26, in which the received signal 29 is multiplied by the original signal from the oscillator 21. If the signals to be multiplied are in phase with each other, the signal indicating the mixer output phase becomes zero. On the other hand, if there is difference in phase, the phase difference signal 27 deviates from zero, and the value of the phase signal 27 depends on the gas content and the consistency. In the gas content measuring, such a frequency is selected advantageously with the oscillator 21 that the output signal 27 of the mixer 26 essentially becomes zero, and as a result, the reference microwave signal 28 and the received microwave signal 29 are at least momentarily in phase with each other. The oscillator 21 is then advantageously controlled by means of the signal 27. In the solution of the invention this frequency is set as the fixed frequency of the microwave signal, and the change in travel time is measured by means of the phase difference between the reference signal 28 indicated by the output signal 27 of the mixer 26 and the received microwave signal 29. The gas content is advantageously measured by calculating the standard deviation of the variation in phase difference between the mixer 26 and the output signal 27, or the like.

The phases of the reference signal 28 and the received signal 29 can be momentarily equalized for the gas content measuring also without changing the frequency, by using an adjustable delay element 30 between the oscillator 21 and the mixer 26. The delay element 30 then changes the reference signal delay from the oscillator 21 in such a manner that the received signal 29 and the reference signal 28 enter the mixer 26 in the same phase at a desired moment, and consequently the output signal 27 becomes effectively zero. By means of the output signal 27 of the mixer 26, the frequency of the oscillator 21 is advantageously controlled, when selecting a convenient frequency, or by means of the output signal 27 the delay element 30 is advantageously controlled for zeroing the phase.

Figure 3A:
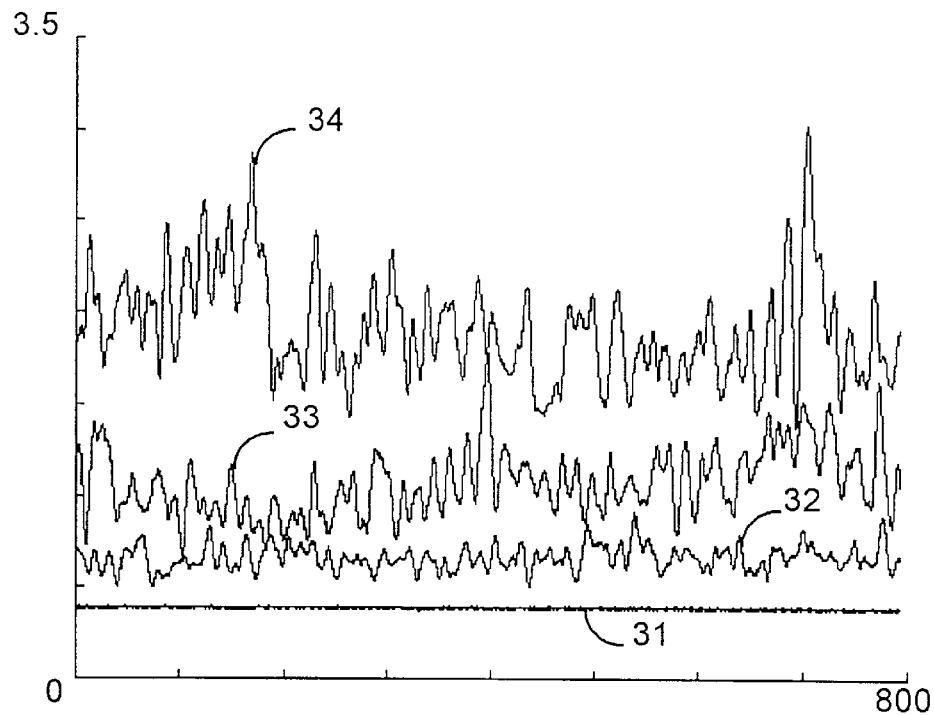
FIG. 3 illustrates phase measurings of a microwave signal in water to which various Quantities of air are added.

FIG. 3 shows measuring results. In FIG. 3, the phase signal 27 is the vertical axis and time is the horizontal axis. A graph 31 describes the behaviour of a phase in clean, air-free water. The graph 31 shows that sheer water does not change the phase of the microwave signal 20 under the effect of pressure variation, and only little noise can be seen in the graph. The graph 32 describes the behaviour of a phase of the microwave signal 20 when some air is added to clean water. Pressure variation generated by the pump 11 shows clearly as phase-change oscillation. As regards the graph 33, some more air is added to water, and the amplitude of the phase oscillation is clearly increased with respect to the graph 32. Further, more air is added to water in the situation described by the graph 34, and as a result, the amplitude of the phase change is further increased. Consequently, the amplitude of the phase oscillation is a function of the gas content.

Figure 4:
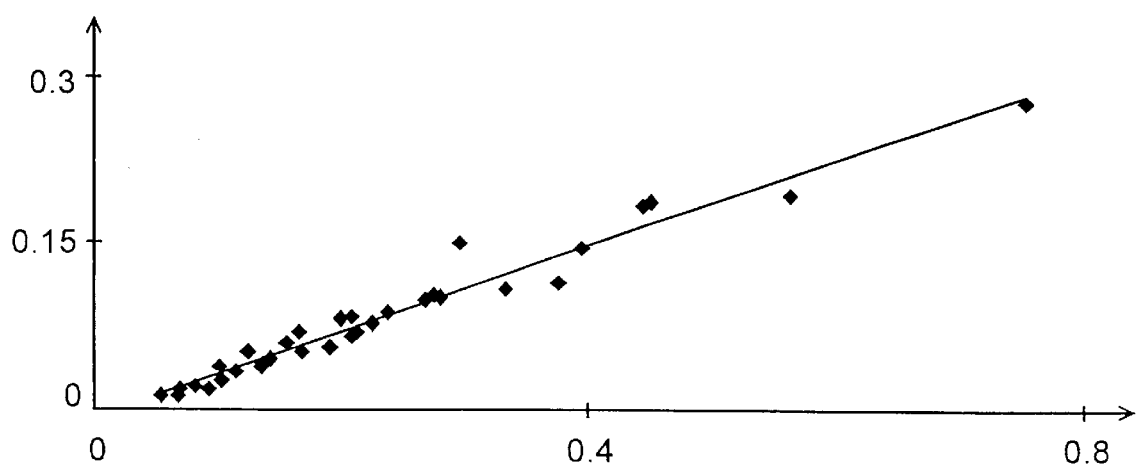
FIG. 4 illustrates the average of a microwave signal phase variation as a function of air content.

FIG. 4 illustrates the measuring of air content in water, in which measuring the standard deviation of the microwave signal phase (vertical axis) is described as a function of the actual air content in water (horizontal axis). Three different flow rates, 15 l/s, 20 l/s and 25 l/s, have been used in the measuring. The measuring points are marked with squares. In FIG. 4, it is observed that the amplitude of the phase variation and the air content preferably have a simple, linear dependence, independent of the flow rate, which dependence can be described by a straight line.

Figure 5:
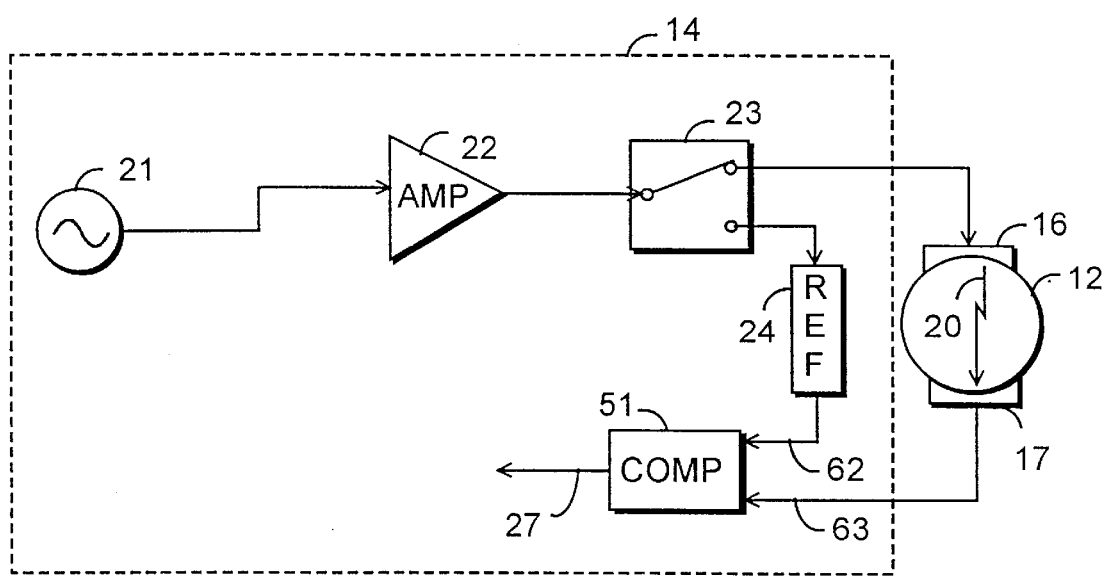
FIG. 5 illustrates a circuitry of a gas content measuring device when attenuation of microwave signal is measured.

FIG. 5 illustrates the measuring of gas content by using attenuation as a variable. The solution is fairly similar to the solution in FIG. 2. In this case, the microwave signal is connected with a switch 23 in turn to the reference channel 24 and the transmitting antenna 16. The strengths of the reference microwave signal 62 and the received signal 63 are measured in the receiver, and the strengths of the received microwave signal 63 and the reference microwave signal 62 are compared with each other in means 51. The comparison is performed, for instance, by calculating the difference or the relationship between the reference signal 62 and the received signal 63. Thereafter the result obtained by the means 51 is transmitted to the means 15, which determine the gas content on the basis of changes in attenuation, for instance, by using the standard deviation or the like.

In the solution of the invention, the pressure variation of the fluid can further be generated by means of a separate pressure modulator 19, in case the pump 11 does not form sufficient pressure pulses. The pressure modulator 19 is, for instance, a diaphragm whose background pressure is variable, a cam or a piston.

The fluid 13 in the solution of the invention is advantageously papermaking pulp in the process duct, and hence the method of the invention is used for measuring the gas content in papermaking pulp to improve the quality of paper before the pulp is fed to the paper machine. The fluid 13 may also be a coating paste used for paper coating.

Even though the invention is described in the above with reference to the example in accordance with the accompanying drawings, it is obvious that the invention is not restricted thereto, but it can be modified in a variety of ways within the scope of the inventive idea disclosed in the appended claims.

We claim:

1. In a method for determining gas content of a fluid in which fluid pressure variations occur, the improvement comprising:

measuring at least one component of a microwave signal that has penetrated through the fluid as the pressure variations occur, the component changing as the pressure variations occur, and determining the gas content of the fluid on the basis of the measured component of the microwave signal.

2. The method as claimed in claim 1, wherein the component of the microwave signal is travel time.

3. The method as claimed in claim 1, wherein the component of the microwave signal is a phase and the measuring comprises:

comparing the phase of the component of the microwave signal with a phase of a reference microwave signal by using a mixer or the like to obtain an output signal;

selecting the phase of the reference microwave signal at a moment such that the output signal substantially becomes zero; and thereafter measuring a phase change of the microwave signal.

4. The method as claimed in claim 3, wherein the gas content is measured as follows:

the phase of the reference microwave signal is changed by means of adjusting frequency, the phase of the received microwave signal is compared with the reference microwave signal by using the mixer, such a frequency is selected for the reference microwave signal of a desired moment that the output signal indicating the phase difference of the mixer, substantially becomes zero, and consequently the reference microwave signal and the received signal are momentarily in phase with each other, and the gas content of the fluid is determined on the basis of changes in the phase of the microwave signal caused by pressure variations.

5. The method as claimed in claim 1, wherein the component of the microwave signal is signal strength and the measuring comprises:

comparing the signal strength of the microwave signal and a signal strength of a reference microwave signal.

6. The method as claimed in claim 1, wherein the measuring the standard deviation of the component.

7. The method as claimed in claim 1, wherein the pressure variations are measured with a separate pressure indicator, and the determining comprises comparing the measured pressure variations with the measured component of the microwave.

8. The method as claimed in claim 1, and further comprising generating the pressure variations of the fluid with a pressure modulator.

9. The method as claimed in claim 1, wherein the fluid is papermaking pulp.

10. The method as claimed in claim 1, wherein the fluid is coating paste.

11. In a device for determining gas content in a fluid in which pressure variations occur with a microwave signal that penetrates through the fluid and has at least one component that changes as the pressure variations occur, the improvements comprising:

means for measuring the at least one component of the microwave signal as the pressure variations occur; and means for determining the gas content in the fluid on the basis of the measuring of the component of the microwave signal.

12. The device as claimed in claim 11, wherein the component is travel time of the microwave signal, and the means for measuring measures the travel time.

13. The device as claimed in claim 11, wherein the component is phase of the microwave signal, and the means for measuring is a mixer or the like that compares the phase of the microwave signal with a reference microwave signal at a moment such that a phase difference is substantially zero and measures the microwave signal on the basis of changes in the phase of the microwave signal thereafter.

14. The measuring device as claimed in claim 11, wherein the component is strength of the microwave signal, and the means for measuring measures the component on the basis of changes in the strength of the microwave signal.

15. The device as claimed in claim 13, wherein the microwave meter is arranged to adjust the phase of the reference microwave signal by changing frequency, to compare the phase of the reference microwave signal with the received signal by using the mixer, to select such a frequency for the microwave signal at a desired moment, that the output signal indicating the phase difference of the mixer, substantially becomes zero, and consequently the reference microwave signal and the received microwave signal are momentarily in phase with each other, and the means for determining the gas content are arranged to measure the gas content in the fluid on the basis of changes in the phase of the microwave signal by using the fixed frequency and phase of the microwave signal.

16. The device as claimed in claim 13, wherein the means for measuring uses the standard deviation of the component.

17. The device as claimed in claim 13, wherein the means for determining measures pressure variations in the fluid with a pressure indicator, and compares results obtained by the pressure indicator with results of the means for measuring to determine the gas content.

18. The device as claimed in claim 13, and further comprising a pressure modulator to generate the pressure variations of the fluid.

19. The device as claimed in claim 13, wherein the fluid is papermaking pulp.

20. The device as claimed in claim 13, wherein the fluid is coating paste.

21. The device as claimed in claim 11, wherein the means for measuring measures the consistency by means of microwaves using frequency modulation measuring based on travel time of the microwaves.

\* \* \* \* \*